United States Patent [19]

Nestor et al.

[11] Patent Number: 4,530,920

[45] Date of Patent: Jul. 23, 1985

[54] NONAPEPTIDE AND DECAPEPTIDE ANALOGS OF LHRH, USEFUL AS LHRH AGONIST

[75] Inventors: John J. Nestor, San Jose; Brian H. Vickery, Cupertino, both of Calif.

[73] Assignee: Syntex (U.S.A.) Inc., Palo Alto, Calif.

[21] Appl. No.: 549,355

[22] Filed: Nov. 7, 1983

[51] Int. Cl.³ .................... C07C 103/52; A61K 37/02
[52] U.S. Cl. .................................. 514/15; 514/800; 260/112.5 R
[58] Field of Search ............... 260/112.5 R, 112.5 LH

[56] References Cited

U.S. PATENT DOCUMENTS

| | | | |
|---|---|---|---|
| 3,773,919 | 11/1973 | Boswell et al. | 424/78 |
| 3,972,859 | 8/1976 | Fujino et al. | 424/177 |
| 4,010,125 | 3/1977 | Schally et al. | 260/112.5 LH |
| 4,215,038 | 7/1980 | Rivier et al. | 260/112.5 R |
| 4,341,767 | 7/1982 | Nestor et al. | 424/177 |

OTHER PUBLICATIONS

Beattie, *J. Am. Med. Chem.*, 18 (No. 12), 1247–1250 (1975).
Horvath et al., *Peptides*, 3, 969–971 (1982) printed in U.S.A.
*Chemical Abstracts*, 88, 631 (1978), Abst. No. 7331j.
Coy et al., *Endocrinology*, 110 (No. 4), 1445–1447 (1982).

*Primary Examiner*—Delbert R. Phillips
*Assistant Examiner*—F. T. Moezie
*Attorney, Agent, or Firm*—Charles L. Hartman; Tom M. Moran; Alan M. Krubiner

[57] ABSTRACT

Synthetic nonapeptide and decapeptide LHRH agonists analogs having a novel gaunadino-substituted, amidine, tertiary or quatrinary aminoacyl residue at position 6 are disclosed herein.

23 Claims, No Drawings

NONAPEPTIDE AND DECAPEPTIDE ANALOGS OF LHRH, USEFUL AS LHRH AGONIST

BACKGROUND OF THE INVENTION

Luteinizing hormone (LH) and follicular stimulating hormone (FSH) are released from the anterior pituitary gland under tne control of the releasing hormone LH-RH produced in the hypothalamic region. LH and FSH act on the gonads to stimulate the synthesis of steroid hormones and to stimulate gamete maturation. The pulsatile release of LH-RH, and thereby the release of LH and FSH, controls the reproductive cycle in domestic animals and humans. Additionally, LH-RH has effects in placenta, in releasing HCG, and directly on the gonads. Agonist analogs of LH-RH are useful for the control of fertility by two mechanisms of action. Low doses of LH-RH analogs can stimulate ovulation and are useful in the treatment of hypothalamic and ovulatory infertility. Additionally they can be used for hypogonadal conditions and impotence, and stimulate spermatogenesis and androgen production in tne male. Paradoxically, larger doses of highly potent and long-lasting analogues of LH-RH have an opposite effect and block ovulation in the female and suppress spermatogenesis in the male. Related to tnese effects is a suppression of normal circulating levels of sexual steroids of gonadal origin, including reduction in accessory organ weight in the male and the female. In domestic animals this paradoxical effect promotes weight gain in a feedlot situation, stimulates abortion in pregnant animals and in general, acts as a chemical sterilant.

The natural mammalian hormone releasing hormone LH-RH is a decapeptide comprised of naturally occuring amino acids (which have the L-configuration except for the achiral amino acid glycine). Its sequence is as follows: (pyro)Glu-His-Trp-Ser-Tyr-Gly-Leu-Arg-Pro-Gly-NH$_2$. Many analogues of this natural material have been studied and the very large majority of them have proven to be of insufficient biological activity to be clinically useful. Certain select modifications have proven to have a beneficial effect on biological activity. By far the most significant modification is obtained by changing the 6-position residue from Gly to a D-amino acid. For example, replacing the Gly residue in the 6-position by D-Ala, D-Leu, D-Phe or D-Trp has led to a series of analogues of LH-RH with increased activity relative to LH-RH. M. Monahan, et al, *Biochem.*, 12, 4616 (1973) for See [D Ala$^6$]-LHRH; J. A. Vilchez-Martinez, et al, *Biochem. Biophys. Res. Comm.*, 59, 1226 (1974) for [D-Leu$^6$]LHRH and desGly$^{10}$ [D-Leu$^6$, Pro$^9$NHET$^{10}$]LHRH; D. H. Coy, et al, *J. Med. Chem.*, 19, 423 (1976) for [D-Phe$^6$]LHRH; and W. Vale, et al, *Clinical Endocrinology, 5th Supp.*, Blackwell Scientific Publications, Oxford, England (1976), p. 2615 and D. H. Coy, et al; *Biochem. Biophys. Res. Comm.*, 67,576 (1979) for [D-Trp$^6$]LHRH.

The structure of piscian (salmon) and avian (chicken) LHRHs are (pryo)-Glu-His-Trp-Ser-Tyr-Gly-Trp-Leu-Pro-GlyNH$_2$ and (pyro)-Glu-His-Trp-Ser-Tyr-Gly-Leu-Gln-Pro-GlyNH$_2$ respectively.

In addition to the substantial increases in activity obtained by the above-referred to substitutions in position 6, further increases in activity may be obtained by eliminating the Gly-NH$_2$ in position 10 to afford a nonapeptide as an alkyl-, cycloalkyl- or fluoroalkylamide, or by replacing Gly-NH$_2$ by an α-azaglycine amide. See for example, M. Fujino, et al, *Biochem. Biophys. Res. Comm.*, 49, 863 (1972), D. H. Coy, et al, *Biochem.* 14, 1848(1975) and A. S. Dutta, et al, *J. Chem. Soc. Perkin I*, 1979, 379.

Substitution of N-methyl-leucine for the leucine residue in position 7 leads to increased stability towards enzymatic degradation. See for example, N. Ling, et al, *Biochem Biophys. Res. Comm.*, 63, 801 (1975).

Substitution of the tryptophan residue in position 3 by 3-(1-naphthyl)-L-alanine leads to an increase in biological potency while 3-(2-naphthyl)-L-alanyl in this position leads to a substantial retention of activity. See for example, K. U. Prasad, et al, *J. Med. Chem.*, 19, 492 (1976) and Y. Yabe, *Chem. Pharm. Bull.*, 24 (12), 3149 (1976).

The tyrosine residue in position 5 can be replaced by phenylalanine or 3-(1-pentafluorophenyl)-L-alanine with the retention of substantial biological activity. See for example, N. Yanaihara, et al, *Biochem. Biophys. Res. Comm.*, 52, 64 (1973), and D. Coy, et al, *J. Med. Chem.*, 16, 877 (1973).

Although some polar 6 postion substituents retain substantial LHRH activity and in some cases are more potent that LHRH, the most potent analogues contain very hydrophobic 6 position substituents. Thus, while [D-LYS$^6$]LHRH (potency 3.8 times LHRH), [D-Arg$^6$]LHRH (potency 3.9 times LHRH), and [D-Arg$^6$, Pro$^9$-NHEt]LHRH (potency 16.7 times LHRH) are active molecules, very hydrophobic analogues such as [D-Trp$^6$]LHRH (potency 36 times LHRH) and [D-Trp$^6$, Pro$^9$-NHEt]LHRH (potency 144 times LHRH) are dramatically more potent. See, for example, J. Rivier, et al., *Peptides-Structure, Function, Biology*, R. Walter and J. Meienhofer, Eds., Ann Arbor Science Publishers, Ann Arbor, MI (1975), p. 863, and W. W. Vale, et al., "Peptides-Structure and Biological Function", E. Gross and J. Meienhofer, Eds., Pierce Chan Co., Rockford, IL (1979), p. 781.

It would be desirable to prepare further analogues of native mammalian, piscian and avian LH-RH which have a high degree of biological activity but higher water solubility than that of those hydrophobic analogues heretofore described.

A series of novel amino acids with strongly basic side chain functionality have been prepared and incorporated into the native LH-RH sequence to yield agonistic LH-RH analogues. These novel amino acids yield highly potent analogues with greater water solubility than the very hydrophobic amino acids previously used to prepare the most potent LH-RH analogs. Some of these amino acids have been recently incorporated into antagonistic LHRH analogues (J. J. Nestor, Jr., et al, Eighth American Peptide Symposium, Tucson, AZ, May 22-27, 1983).

SUMMARY OF THE INVENTION

The present invention refers to novel nonapeptide and decapeptide derivatives of LH-RH which have, in the 6-position, certain positively charged hydrophilic D-amino acids. The invention is also directed to various methods of use of these compounds and to pharmaceutical compositions therefor. A further aspect of the invention involves processes for the preparation of the novel compounds described above and to intermediates useful in such processes.

DETAILED DESCRIPTION OF THE INVENTION

Description of the Analogs

The present invention relates to novel nonapeptide and decapeptide analogs of LHRH which have the formula

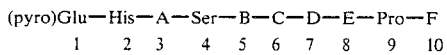

(I)

and the pharmaceutically acceptable salts thereof, wherein:

A is tryptophyl, phenylalanyl, 3-(1-naphtnyl)-L-alanyl or 3-(2-napthyl)-L-alanyl;

B is tyrosyl, phenylalanyl or 3-(1-pentafluorophenyl)-L-alanyl;

C is an amino acyl residue selected from the group consisting of the radicals represented by the following structural formulas:

(a)

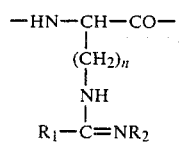

(II)

wherein
n is 1 to 5;

$R_1$ is alkyl of 1 to 12 carbon atoms, $-NRR_3$ wherein R is hydrogen or alkyl of 1 to 4 carbon atoms, $R_3$ is hydrogen, alkyl of 1 to 12 carbon atoms, cycloalkyl, fluoroalkyl, phenyl, benzyl, $-(CH_2)_n$-morpholino or $-(CH_2)_nN(R_4)_2$ wherein n is 1 to 5 and $R_4$ is lower alkyl;

$R_2$ is hydrogen or $R_3$; or $R_1$ and $R_2$ comprise a ring represented by the following structural formulas:

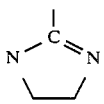

IIA

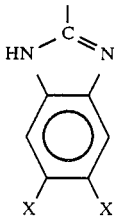

IIB

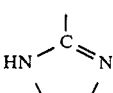

IIC

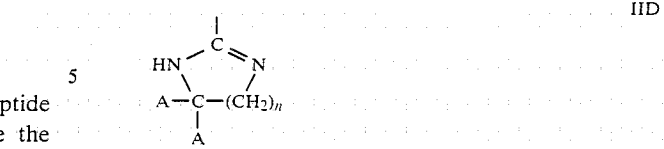

IID wherein n is 1 to 7; A is hydrogen, alkyl of 1 to 6 carbon atoms or cycloalkyl; and X is halo or A or (b)

(III)

wherein $R_5$ is alkyl of 1 to 6 carbon atoms, benzyl, phenylethyl, cyclohexyl, cyclopentyl; and $R_6$, $R_7$ and $R_8$ are hydrogen or alkyl of 1 to 4 carbon atoms; and n is the integer 2–5; or (c) a substituent of the formula

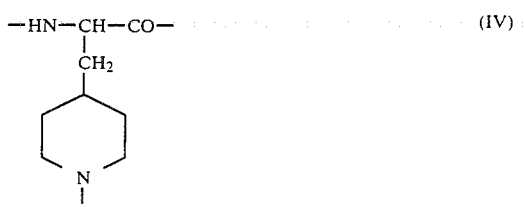

(IV)

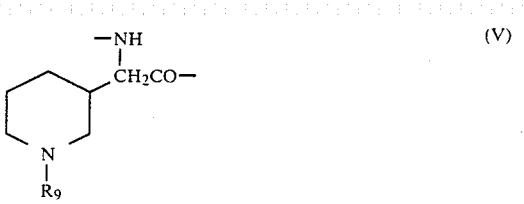

(V)

wherein $R_9$ is hydrogen, alkyl of 1 to 12 carbon atoms, phenyl or phenylloweralkyl;

D is leucyl, isoleucyl, nor-leucyl, N-methyl-leucyl or tryptophanyl;

E is arginyl or leucyl; and

F is glycinamide or $-NH-R^1$, wherein
$R^1$ is lower alkyl, cycloalkyl, fluro lower alkyl or $-NH-CO-NH-R^2$ wherein $R^2$ is hydrogen or lower alkyl.

As set forth above and for convenience in describing this invention, the conventional abbreviations for the various common amino acids are used as generally accepted in the peptide art as recommended by the IUPAC-IUB Commission on Biochemical Nomenclature, *Biochemistry*, 11, 1726 (1972) and represent L-amino acids with the exception of the achiral amino acid glycine and with the further exception of the amino acids in the 6-position designated by C. All peptide sequences mentioned herein are written according to the generally accepted convention whereby the N-terminal amino acid is on the left and the C-terminal amino acid is on the right.

As used herein, the term "pharmaceutically acceptable salts" refer to salts that retain the desired biological activity of the parent compound and do not impart any undesired toxicological effects. Examples of such salts are (a) acid addition salts formed with inorganic acids, for example hydrochloric acid, hydrobromic acid, sulfuric acid, phosphoric acid, nitric acid and the like; and salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, pamoic acid, alginic acid, polyglutamic acid, naphthalenesulfonic acids, naphthalenedisulfonic acids, polygalacturonic acid; (b) salts with polyvalent metal cations such as zinc, calcium, bismuth, barium, magnesium, aluminum, copper, cobalt, nickel, cadmium, and the like; or with an organic cation formed from N,N'-dibenzylethylene-diamine or ethylenediamine; or (c) combinations, of (a) and (b), e.g. a zinc tannate salt and the like.

As used herein the term "lower alkyl" refers to a straight or branched chain saturated hydrocarbon group having from 1 to 4 carbon atoms such as, for example, methyl, ethyl, n-propyl, isopropyl, n-butyl, isobutyl, sec-butyl and tert-butyl; the term "cycloalkyl group" refers to a cyclic saturated hydrocarbon group having from 3 to 6 carbon atoms, for example cyclopropyl, cyclobutyl, cyclopentyl and cyclohexyl; the term "fluoro lower alkyl" refers to a lower alkyl group wherein one or more hydrogen atoms are replaced by fluorine, such as, for example, trifluoromethyl, pentafluoroethyl, 2,2,2-trifluoroethyl, and the like.

Certain other abbreviations will be useful in describing the invention. The present invention employs replacements by amino acids which do not occur in nature. Particularly commonly employed among these are the following:

| Amino Acid Residue | Abbreviation |
|---|---|
| 3-(2-naphthyl)-D-alanyl | D-Nal(2) |
| 3-(p-fluorophenyl)-D-alanyl | D-p-F—Phe |
| 3-(p-chlorophenyl)-D-alanyl | D-p-Cl—Phe |
| D-homoarginyl | D-Har |
| N,N'—guanidino-dimethyl-D-homoarginyl | D-Dmh |
| N,N'—guanidino-diethyl-D-homoarginyl | D-Deh |
| N,N'—guanidino-dipropyl-D-homoarginyl | D-Dph |
| N,N'—guanidino-diisopropyl-D-homoarginyl | D-Dih |
| N,N'—guanidino-dibutyl-D-homoarginyl | D-Dbh |
| N,N'—guanidino-dihexyl-D-homoarginyl | D-Dhh |
| N—guanidino-ethyl-D-homoarginyl | D-Eth |
| N—guanidino-propyl-D-homoarginyl | D-Prh |
| N—guanidino-isopropyl-D-homoarginyl | D-Iph |
| N—guanidino-heptyl-D-homoarginyl | D-Hha |
| N,N'—guanidino-dicyclohexyl-D-homoarginyl | D-Dch |
| N,N'—guanidino-diisopropyl-D-arginyl | D-Dia |
| N,N'—guanidino-dicyclohexyl-D-arginyl | D-Dca |

The following structure

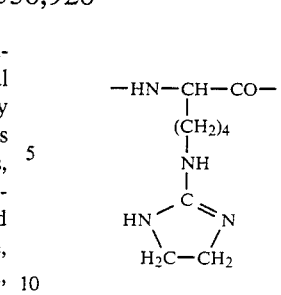

is represented by the abbreviation D-Eth.

Preferred compounds of this invention are those wherein X is

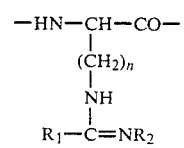

wherein n is 4 (homoargininyl); $R_1$ is $NRR_3$ wherein R is hydrogen and $R_3$ is hydrogen, alkyl of 1 to 6 carbon atoms, cycloalkyl, or fluoroalkyl; and $R_2$ is alkyl of 1 to 12 carbon atoms, cycloalkyl or fluoroalkyl, or $R^1$ and $R^2$ together form a ring represented by the structural formula:

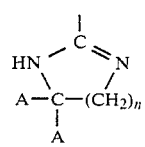

IID wherein n is 1 to 3 and A is hydrogen.

More preferred are those compounds wherein the R substituents on X are as follows: $R_2$ and $R^3$ are the same and are methyl, ethyl, butyl, hexyl, or n in formula IID is 1.

Most preferred are:
(pyro)Glu-L-His-L-Trp-L-Ser-L-Tyr-D-Eth-L-Leu-L-Arg-L-ProNHET;
(pyro)Glu-L-His-L-Trp-L-Ser-L-Tyr-D-Deh-L-Leu-L-Arg-L-ProNHET;
(pyro)Glu-L-His-L-Trp-L-Ser-L-Tyr-D-Deh-L-Leu-L-Gln-L-Pro-NH$_2$;
(pyro)Glu-L-His-L-Trp-L-Ser-L-Tyr-D-Deh-L-Leu-L-Gln-L-Pro-NHEt;
(pyro) Glu-L-His-L-Trp-L-Ser-L-Tyr-D-Deh-L-Trp-L-Leu-L-Pro-NH$_2$;
(pyro)Glu-L-His-L-Trp-L-Ser-L-Tyr-D-Deh-L-Trp-L-Leu-L-Pro-NHEt;
(pyro)Glu-L-His-L-Trp-L-Ser-L-Tyr-D-Dhh-L-Leu-L-Arg-L-ProNHET;
(pyro)Glu-L-His-L-Trp-L-Ser-L-Tyr-D-Deh-L-MeLeu-L-Arg-L-ProNHET;
(pyro)Glu-L-His-L-Nal(2)-L-Ser-L-Tyr-D-Deh-L-Leu-L-Arg-L-ProNHET;
(pyro)Glu-L-His-L-Trp-L-Ser-L-Tyr-D-Deh-L-Leu-L-Arg-L-Pro-GlyNH$_2$;
(pyro)Glu-L-His-L-Trp-L-Ser-L-Tyr-D-Deh-L-MeLeu-L-Arg-L-Pro-GlyNH$_2$; and
(pyro)Glu-L-His-L-Nal(2)-L-Ser-L-Tyr-D-Deh-L-MeLeu-L-Arg-L-Pro-GlyNH$_2$.

The compounds of this invention and, particularly, the salts thereof, exhibit surprisingly potent and long lasting LH-RH agonist activity in comparison to the previously most potent hydrophilic LH-RH agonist, namely (pyro)Glu-His-Trp-Ser-Tyr-D-Arg-Ser-Arg-Pro-Gly-NH$_2$ and the corresponding prolylethylamide. A primary measure of potency is the ability to partially or completely suppress estrus in normally cycling adult female rats (determined over a 2 week period) by twice daily subcutaneous injection.

Other bioassays which have been used for LH-RH analogues and which may be used for compounds of the present invention include:

(a) ovulation induction in diestrous or proestrous female rats by subcutaneous injection (Rippel, et al, *Proc. Soc. Exp. Biol. Med.*, 148, 1193(1975)), (b) LH and FSH release by dispersed anterior pituitary cell cultures as measured by radioimmunoassay (Vale, et al, *Endocrinology*, 91, 562(1972)), and (c) LH and FSH release into the peripheral circulation of ovariectomized, steroid treated rats in response to intravenous injection as measured by radioimmunoassay (Arimura, et al, *Endocrinology*, 90, 163(1972)).

On a more advanced level, activity for these compounds may be demonstrated in vivo by depression of spermatogenesis and circulating and testicular levels of testosterone as well as dramatic reduction in prostate size in dogs suffering from benign prostatic hypertrophy.

As a result of the above the compounds may find use in a large variety of situations where control of LH and FSH, or direct gonadal action is important, including:

Physiological Utilities (Low Dose Effects)

ovulation induction in anovulatory infertility and for timed ovulation in female mammals;
therapy for infertility due to insufficient luteal function in women;
therapy for hypogonadotrophic or hypogonadal infertility in either sex-human.
therapy for cystic ovary/nymphomania syndrome in cattle;
induction or enhancement of sexual behaviour or therapy for impotence/frigidity.

Paradoxical Utilities (High Dose Effects)

female contraception;
ovulation suppression or delay;
induction of parturition;
synchronization of ovulation;
estrus suppression;
growth promotion in female animals;
luteolysis, menses induction;
early, first trimester abortifacient;
therapy for endometriosis;
therapy for mammary tumors and cysts
therapy for polycystic ovary syndrome (Stein-Leventhal);
therapy for uterine carcinoma;
therapy for benign prostatic hypertrophy and for prostatic carcinoma;
male contraception;
therapy for diseases which result from excessive gonadal hormone production in either sex;
lowering, blocking or abolishing gonadal steroid output;
functional castration in male food producing animals; and
suppression of proestrous discharge.

Another aspect of the present invention relates to particular uses for the above-described compounds, (including uses not heretofore described for LH-RH analogues) namely their uses for inhibiting ovulation (i.e. contraception) in the female, in the management of endometriosis, in the treatment of benign prostatic hypertrophy and in the inhibition of spermatogenesis (i.e. contraception) in the male. Thus, in these aspects, the invention is directed to a method useful for inhibition of ovulation, management of endometriosis, reduction of prostate size or inhibition of spermatogenesis in a mammalian subject having need of or desiring, said treatment which comprises administering to said subject an effective amount of a compound of the present invention as hereinabove described or a pharmaceutical composition containing same.

In the practice of the method of this invention an effective amount of a compound of the invention or a pharmaceutical composition containing same is administered to the subject in need of, or desiring, such treatment. These compounds or compositions may be administered by any of a variety of routes depending upon the specific end use, including orally, parenterally (including subcutaneous, intramuscular and intravenous administration), vaginally (particularly for contraception), rectally, buccally (including sublingually), or intranasally. The most suitable route in any given case will depend upon the use, particular active ingredient, the subject involved, and the judgment of the medical practitioner. The compound or composition may also be administered by means of slow-release, depot or implant formulations as described more fully hereinbelow.

In general for the uses hereinabove described, which are so-called "paradoxical" or high-dose uses, it is expedient to administer the active ingredient in amounts between about 0.01 and 100 ug/kg body weight per day, preferably between about 0.1 and 10.0 ug/kg body weight per day. This administration may be accomplished by a single daily administration, by distribution over several applications or by slow release in order to achieve the most effective results.

The exact dose and regimen for administration of these compounds and compositions will necessarily be dependent upon the needs of the individual subject being treated, the type of treatment, the degree of affliction or need and, of course, the judgment of the medical practitioner. In general, parenteral administration requires lower dosage than other methods of administration which are more dependent upon absorption.

A further aspect of the present invention relates to pharmaceutical compositions containing as active ingredient a compound of the present invention which compositions comprise such compound in admixture with a pharmaceutically acceptable, non-toxic carrier. As mentioned above, such compositions may be prepared for use for parenteral (subcutaneous, intramuscular or intravenous) administration particularly in the form of liquid solutions or suspensions; for use in vaginal or rectal administration particularly in semisolid forms such as creams and suppositories; for oral or buccal administration particularly in the form of tablets or capsules; or intranasally particularly in the form of powders, nasal drops or aerosols.

The compositions may conveniently be administered in unit dosage form and may be prepared by any of the methods well-known in the pharmaceutical art, for example as described in Remington's Pharmaceutical Sciences, Mack Publishing Company, Easton, Pa., 1970. Formulations for parenteral administration may contain as common excipients sterile water or saline, polyalkylene glycols such as polyethylene glycol, oils of vegetable origin, hydrogenated naphthalenes and the like. Formulations for vaginal or rectal administration, e.g. suppositories, may contain as excipients, for example, polyalkyleneglycols, vaseline, cocoa butter, and the like. Vaginal formulations may contain absorption enhancing agents such as bile salts, salts of ethylenediamine, citrates or the like. Formulations for inhalation administration may be solid and contain as excipients, for example, lactose or may be aqueous or oily solutions for administration in the form of nasal drops. For buccal administration typical excipients include sugars, calcium stearate, magnesium stearate, pregelatinated starch, and the like.

It is particularly desirable to deliver the compounds of the present invention to the subject over prolonged periods of time, for example, for periods of one week to one year from a single administration. Various slow release, depot or implant dosage forms may be utilized. For example, a dosage form may contain a pharmaceutically acceptable non-toxic salt of the compound which has a low degree of solubility in body fluids, for example, (a) an acid addition salt with a polybasic acid such as phosphoric acid, sulfuric acid, citric acid, tartaric acid, tannic acid, pamoic acid, alginic acid, polyglutamic acid, naphthalene mono- or di-sulfonic acids, polygalacturonic acid, and the like; (b) a salt with a polyvalent metal cation such as zinc, calcium, bismuth, barium, magnesium, aluminum, copper, cobalt, nickel, cadmium and the like, or with an organic cation formed from e.g., N,N'-dibenzylethylenediamine or ethylenediamine; or (c) combinations of (a) and (b) e.g. a zinc tannate salt. Additionally, the compounds of the present invention or, preferably, a relatively insoluble salt such as those just described, may be formulated in a gel, for example, an aluminum monostearate gel with, e.g. sesame oil, suitable for injection. Particularly preferred salts are zinc salts, zinc tannate salts, pamoate salts, and the like. Another type of slow release depot formulation for injection would contain the compound or salt dispersed or encapsulated in a slow degrading, non-toxic, non-antigenic polymer such as a polylactic acid/polyglycolic acid polymer for example as described in U.S. Pat. No. 3,773,919. The compounds or, preferably, relatively insoluble salts such as those described above may also be formulated in cholesterol matrix silastic pellets, particularly for use in animals. Additional slow release, depot or implant formulations, e.g. liposomes, are well known in the literature. See, for example, "Sustained and Controlled Release Drug Delivery Systems", J. R. Robinson ed., Marcel Dekker, Inc., New York, 1978. Particular reference with respect to LH-RH type compounds may be found, for example, in U.S. Pat. No. 4,010,125.

Additionally, the compounds of this invention may be administered as a nasal spray. Such formulations preferably will contain surfactants to enhance peptide absorption. For example, incorporation of surfactants such as etnylenediamine salts and bile acids and their salts into nasal formulations in amounts of about 0.02–10%, will enhance the amount of peptide passing through the mucus membrane.

The polypeptides of the present invention may be synthesized by any techniques that are known to those skilled in the peptide art. An excellent summary of the many techniques so available may be found in J. M. Stewart and J. D. Young, "Solid Phase Peptide Synthesis", W. H. Freeman Co., San Francisco, 1969, and J. Meienhofer, "Hormonal Proteins and Peptides", Vol. 2, p. 46., Academic Press (New York), 1973 for solid phase peptide synthesis and E. Schroder and K. Lubke, "The Peptides", Vol. 1, Academic Press (New York), 1965 for classical solution synthesis.

In general, these methods comprise the sequential addition of one or more amino acids or suitably protected amino acids to a growing peptide chain. Normally, either the amino or carboxyl group of the first amino acid is protected by a suitable protecting group. The protected or derivatized amino acid can then be either attached to an inert solid support or utilized in solution by adding the next amino acid in tne sequence having the complimentary (amino or carboxyl) group suitably protected, under conditions suitable for forming the amide linkage. The protecting group is then removed from this newly added amino acid residue and the next amino acid (suitably protected) is then added, and so forth. After all the desired amino acids have been linked in the proper sequence, any remaining protecting groups (and any solid support) are removed sequentially or concurrently, to afford the final polypeptide. By simple modification of this general procedure, it is possible to add more than one amino acid at a time to a growing chain, for example, by coupling (under conditions which do not racemize chiral centers) a protected tripeptide with a properly protected dipeptide to form, after deprotection, a pentapeptide.

A particularly preferred method of preparing compounds of the present invention involves solid phase peptide synthesis.

In this particularly preferred method the α-amino function of the amino acids is protected by an acid or base sensitive group. Such protecting groups should have the properties of being stable to the conditions of peptide linkage formation, while being readily removable without destruction of the growing peptide chain or racemization of any of the chiral centers contained therein. Suitable protecting groups are t-butyloxycarbonyl (Boc), benzyloxycarbonyl (Cbz), biphenylisopropyloxycarbonyl, t-amyloxycarbonyl, isobornyloxycarbonyl, 1,1-dimethyl-3,5-dimethoxybenzyloxycarbonyl, o-nitrophenylsulfenyl, 2-cyano-t-butyloxycarbonyl, 9-fluorenylmethyloxycarbonyl and the like, especially t-butyloxycarbonyl (Boc).

Particularly preferred side chain protecting groups are, for arginine:nitro, p-toluenesulfonyl, 4-methoxybenzenesulfonyl, Cbz, Boc and adamantyloxycarbonyl; for tyrosine: benzyl, o-bromobenzyloxycarbonyl, 2,6-dichlorobenzyl, isopropyl, cyclohexyl, cyclopentyl and acetyl; for serine: benzyl, acetyl, and tetrahydropyranyl; for histidine: benzyl, p-toluenesulfonyl and 2,4-dinitrophenyl; for tryptophan: formyl.

Tne C-terminal amino acid is attached to a suitable solid support. Suitable solid supports useful for the above synthesis are those materials which are inert to the reagents and reaction conditions of the stepwise condensation-deprotection reactions, as well as being insoluble in the media used. Suitable solid supports are chloromethylpolystyrene-divinylbenzene polymer, hydroxymethyl-polystyrene-divinylbenzene polymer functionalized, cross-linked poly-N-acrylylpyrrolidine resins, and the like, especially chloromethyl-polystyrene-1% divinylbenzene polymer. For the special case where the C-terminus of the compound will be glycinamide, a particularly useful support is the benzhydrylaminopolystyrene-divinylbenzene polymer described by P. Rivaille, et al, *Helv. Chim. Acta.*, 54, 2772 (1971). The attachment to the chloromethyl polystyrenedivinylbenzene type of resin is made by means of the reaction of the $N^1$-protected amino acid, especially the Boc-amino acid, as its cesium, tetramethylammonium, triethylammonium, 4,5-diazabicyclo-[5.4.0]undec-5-ene, or similar salt in ethanol, acetonitrile, N,N-dimethylformamide (DMF), and the like, especially its cesium salt in DMF, with the chloromethyl resin at an elevated temperature, for example between about 40° and 60° C., preferably about 50° C., for from about 12 to 48 hours, preferably about 24 hours. The $N^\alpha$-Boc-amino acid is attached to the benzhydrylamine resin by means of an N,N'-dicyclohexylcarbodiimide (DCC)/1-hydroxybenzotriazole (HBT) mediated coupling for from about 2 to about 24 hours, preferably about 12 hours at a temperature of between about 10° and 50° C., preferably 25° C., in a solvent such as dichloromethane or DMF, preferably dichloromethane. The coupling of successive protected amino acids can be carried out in an automatic polypeptide synthesizer as is well known in the art. The removal of the $N^1$-protecting groups may be performed in the presence of, for example, a solution of trifluoroacetic acid in methylene chloride, hydrogen chloride in dioxane, hydrogen chloride in acetic acid, or other strong acid solution, preferably 50% trifluoroacetic acid in dichloromethane at about ambient temperature. Each protected amino acid is preferably introduced in approximately 2.5 molar excess and the coupling may be carried out in dichloromethane, dichloromethane/DMF mixtures, DMF and the like, especially in methylene chloride at about ambient temperature. The coupling agent is normally DCC in dichloromethane but may be N,N'-di-iso-propylcarbodiimide or other carbodiimide either alone or in the presence of HBT, N-hydroxysuccinimide, other N-hydroxyimides or oximes. Alternately, protected amino acid active esters (e.g. p-nitrophenyl, pentafluorophenyl and the like) or symmetrical anhydrides may be used.

At the end of the solid phase synthesis the fully protected polypeptide is removed from the resin. When the linkage to the resin support is of the benzyl ester type, cleavage is by means of aminolysis with an alkylamine or fluoroalkylamine for peptides with a proline C-terminus, or by aminolysis with, for example, ammonia/methanol or ammonia/ethanol for peptides with a glycine C-terminus at a temperature between about 10° and 50° C., preferably about 25° C., for between about 12 and 24 hours preferably about 18 hours. Alternatively, the peptide may be removed from the resin by transesterification, e.g., with methanol, followed by aminolysis or by HF/anisole treatment to yield the free acid C-terminus (e.g., —Pro—OH). The protected peptide may be purified at this point by silica gel chromatography. The removal of the (side chain) protecting groups from the polypeptide is performed by treating the aminolysis product with, for example, anhydrous liquid hydrogen fluoride in the presence of anisole or other carbonium scavenger, treatment with hydrogen fluoride/pyridine complex, treatment with tris(trifluoroacetyl)boron and trifluoroacetic acid, by reduction with hydrogen and palladium on carbon or polyvinylpyrrolidone, or by reduction with sodium in liquid ammonia, preferably with liquid hydrogen fluoride, and anisole at a temperature between about −10° and +10° C., preferably about 0° C., for between about 15 minutes and 1 hour, preferably about 30 minutes. For the glycine terminal peptides on the benzhydrylamine resins, the resin cleavage and deprotection steps may be combined in a single step utilizing liquid hydrogen fluoride and anisole as described above. The fully deprotected polypeptide is then purified by a sequence of chromatographic steps employing any or all of the following types: ion exchange on a weakly basic resin in the acetate form; gel permeation chromatography, e.g. on Sephadex G-25; hydrophobic adsorption chromatography on underivatized polystyrene-divinylbenzene (for example Amberlite XAD); silica gel adsorption chromatography; ion exchange chromatography on carboxymethylcellulose; partition chromatography, e.g. on Sephadex G-25, or countercurrent distribution; high performance liquid chromatography (HPLC), especially reverse phase HPLC on octyl- or octadecylsilyl-silica bonded phase column packing.

If a racemic amino acid is used in the 6-position, tne diastereomeric nonapeptide or decapeptide final products are separated, and the desired peptide containing a D-amino acid in the 6-position is isolated and purified, preferably during the above-described chromatographic process.

The preparation of peptides having C-terminal azaglycine amides may be performed using classical peptide solution synthesis using known peptide intermediates. This preparation is best performed by coupling the corresponding nonapeptide acid (free peptide-Pro-OH C-terminus) with semi-carbazide.HCl in the presence of DCC/HBT.

Thus, in another aspect the present invention relates to a method for preparing compounds of the formula

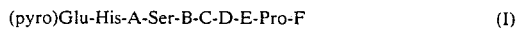

(pyro)Glu-His-A-Ser-B-C-D-E-Pro-F      (I)

and the pharmaceutically acceptable salts thereof wherein:

A is tryptophyl, phenylalanyl, 3-(1-naphthyl)-L-alanyl or 3-(2-napthyl)-L-alanyl;

B is tyrosyl, phenylalanyl or 3-(1-pentafluorophenyl)-L-alanyl;

C is an amino acyl residue selected from the group consisting of the radicals represented by the following structural formulas:

(a)

$$\begin{array}{c} -HN-CH-CO- \\ | \\ (CH_2)_n \\ | \\ NH \\ | \\ R_1-C=NR_2 \end{array} \quad (II)$$

wherein
n is 1 to 5;
$R_1$ is alkyl of 1 to 12 carbon atoms, —$NRR_3$ wherein R is hydrogen or alkyl of 1 to 4 carbon atoms, $R_3$ is hydrogen, alkyl of 1 to 12 carbon atoms, cycloalkyl, fluoroalkyl, phenyl, benzyl, —$(CH_2)_n$-morpholino or —$(CH_2)_nN(R_4)_2$ wherein n is 1 to 5 and $R_4$ is lower alkyl;

$R_2$ is hydrogen or $R_3$; or $R_1$ and $R_2$ comprise a ring represented by the following structural formulas:

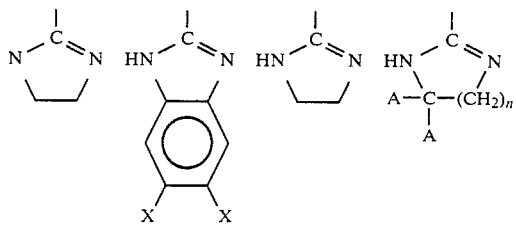

wherein n is 1 to 7; A is hydrogen, alkyl of 1 to 6 carbon atoms or cycloalkyl; and X is halo or A or (b)

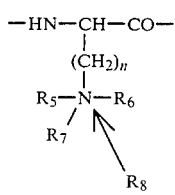

wherein $R_5$ is alkyl of 1 to 6 carbon atoms, benzyl, phenylethyl, cyclohexyl, cyclopentyl; and $R_6$, $R_7$ and $R_8$ are hydrogen or alkyl of 1 to 4 carbon atoms; and n is the integer 2-5; or (c) a substituent of the formula

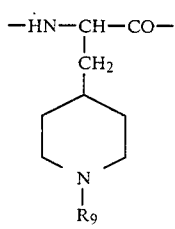

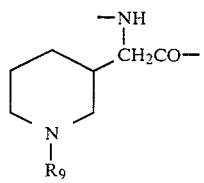

wherein $R_9$ is hydrogen, alkyl of 1 to 12 carbon atoms, phenyl or phenylloweralkyl;

D is leucyl, isoleucyl, nor-leucyl or N-methyl-leucyl;

Z is glycinamide or —NH—$R^1$, wherein $R^1$ is lower alkyl, cycloalkyl, fluoro lower alkyl or

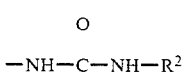

wherein $R^2$ is hydrogen or lower alkyl.

which process comprises:

(i) removing protecting groups and, optionally, covalently bound solid support from a protected polypeptide to afford a compound of Formula (I) or a salt thereof, and optionally (ii) converting a compound of Formula (I) to a pharmaceutically acceptable salt, or (iii) converting a salt of a compound of Formula (I) to a pharmaceutically acceptable salt, or (iv) decomposing a salt of a compound of Formula (I) to a free polypeptide of Formula (I).

The following examples are given to enable those skilled in the art to more fully understand and practice the present invention. They should not be construed as a limitation upon the scope of the invention, but merely as being illustrative and representative thereof.

Preparation A

A mixture of 5.24 g of benzyl $N^\alpha$-benzyloxycarbonyl-D-lysinate toluenesulfonate (B. Bezus and L. Zervas, J. Am. Chem. Soc. 83, 719 (1961)) and 1.72 ml of diisopropylethylamine in 60 ml of dioxane is treated with 1.89 g of N,N'-diisopropylcarbodiimide. The reaction mixture is stirred at 100° C. for 6 hours, cooled to room temperature and concentrated to a solid. The solid is suspended in 20 ml of warm DMF, filtered to remove N,N'-diisopropylurea and the filtrate concentrated to a solid. Benzyl $N^\alpha$-benzyloxycarbonyl-N,N'-guanidinodiisopropyl-D-homoargininate toluenesulfonate is obtained as a white solid by crystallization from methanol/ethyl acetate $[\alpha]_D -7.26°$ (C 0.3, MeOH).

Similarly, by using the above procedure, but substituting:

N,N'-dicyclohexylcarbodiimide;
N,N'-di-n-hexylcarbodiimide;
N,N'-diethylcarbodiimide;
N,N'-di-n-propylcarbodiimide;
N,N'-di-i-propylcarbodiimide;
N,N'-di-n-butylcarbodiimide;
N,N'-dimethylcarbodiimide;
N,N'-di-i-butylcarbodiimide;
N,N'-di-n-pentylcarbodiimide;
N,N'-di-i-pentylcarbodiimide;
N,N'-diphenylcarbodiimide;
N,N'-ditolylcarbodiimide; or
1-(3-dimethylaminopropyl)-3-ethylcarbodiimide-HCl
and the like, there are obtained:

benzyl $N^\alpha$-benzyloxycarbonyl-N,N'-guanidinodicyclohexyl-D-homoargininate, $[\alpha]_D 8.07°$ (C 0.9 MeOH);

benzyl $N^\alpha$-benzyloxycarbonyl-N,N'-guanidinodiethyl-D-homoargininate, $[\alpha]_D^{25} 12.9°$ (C 0.1, MeOH);

benzyl $N^\alpha$-benzyloxycarbonyl-N,N'-guanidinodi-n-propyl-D-homoargininate $[\alpha]_D 10.9°$ (C 0.8 MeOH);

benzyl $N^\alpha$-benzyloxycarbonyl-N,N'-guanidinodiisopropyl-D-argininate, $[\alpha]_D -4.71°$ (C 1.0, MeOH);

benzyl $N^\alpha$-benzyloxycarbonyl-N,N'-guanidinon-propyl-D-homoargininate;

benzyl $N^\alpha$-benzyloxycarbonyl-N,N'-guanidinodi-n-butyl-D-homoargininate, $[\alpha]_D^{25} 10.7°$ (C 0.6, MeOH);

benzyl $N^\alpha$-benzyloxycarbonyl-N,N'-guanidinodi-i-butyl-D-homoargininate;

benzyl $N^\alpha$-benzyloxycarbonyl-N,N'-guanidinodi-n-pentyl-D-homoargininate;

benzyl $N^\alpha$-benzyloxycarbonyl-N,N'-guanidinodi-phenyl-D-homoargininate, $[\alpha]_D^{25} 4.25°$ (C 0.4, MeOH);

benzyl $N^\alpha$-benzyloxycarbonyl-N,N'-guanidinodimethyl-D-homoargininate;

benzyl $N^\alpha$-benzyloxycarbonyl-N,N'-guanidinodi-n-hexyl-D-homoargininate, $[\alpha]_D^{25} 10.1°$ (C 0.4,MeOH);

benzyl $N^\alpha$-benzyloxycarbonyl, N-guanidino-(3-dimethylaminopropyl)-N'-guanidino-ethyl-D-homoargininate, $[\alpha]_D^{25} 11.7°$ (C 0.4, MeOH) as their toluenesulfonate salts.

Similarly, by substituting benzyl N$^\alpha$-benzyloxycarbonyl-D-ornithinate for the D-lysinate there may be obtained the corresponding arginine analogs as their toluenesulfonate salts, for example:

benzyl N$^\alpha$-benzyloxycarbonyl-N,N'-guanidino-dimethyl-D-argininate;
benzyl N$^\alpha$-benzyloxycarbonyl-N,N'-guanidino-di-i-propyl-D-argininate; $[\alpha]_D^{25}$ 14.7° (C 0.4, MeOH);
benzyl N$^\alpha$-benzylcarbonyl-N,N'-guanidino-diethyl-D-arginate, and the like.

PREPARATION B (i) Benzyl N$^\alpha$-benzyloxycarbonyl-N$^G$,N$^{G'}$-ethano-D-homoargininate To a mixture of 15 ml of toluene and 15 ml of t-BuOH was added 2.71 g of benzyl N$^\alpha$-benzyloxycarbonyl-D-lysinate and 1.46 g of 2-methylthioimidazoline.HI (available from Aldrich). The pH of the mixture was brought to .8 by the additioh of diisopropylethylamine and the solution heated under reflux for 24 hours.

The solution was concentrated in vacuo and the residue was loaded on a silica gel column (250 g). The column was eluted with a gradient from CH$_2$Cl$_2$/MeOH (19:1) to CH$_2$Cl$_2$/MeOH (7:3). The fractions containing product were detected by TLC, pooled, and concentrated to dryness, 2.9 g of white foam.

A 2 g portion of the above-named product was dissolved in 50 ml of EtOH containing 0.8 g of 10% Pd/C. The solution was stirred under H$_2$ for 8 hours. The mixture was filtered on Celite and the filtrate was concentrated to dryness to give N$^G$,N$^{G'}$-ethano-D-homoarginine as a white foam, 1.2 g.

(ii) N$^\alpha$-Boc-N$^G$,N$^{G'}$-ethano-D-homoarginine

```
        H
        |
   BocN—CH—COOH
        |
       (CH2)4
        |
        N
        |
       /C\
     HN    N
       \__/
```

A solution of 2.74 g of D-lysine dihydrocnloride and 4.03 g of 2-methylthio-2-imidazoline.hydroiodide in 16.5 ml of 2N NaOH was stirred at room temperataure for 6 days. Analysis of the reaction mixture on an amino acid analyzer showed that ~70% of the desired ε-dialkylguanidino compound had been formed. A further 0.25 g of the 2-methylthio-2-imidazoline.hydroiodide and 1 ml of 2N NaOH were added and the reaction was continued at room temperature for 3 more days.

The reaction mixture was treated with 0.8 g MgO and 4.36 g of di-tert-butyldicarbonate in 20 ml of dioxane. The pH was adjusted to 9.5 with 1N NaOH. After overnight reaction some starting material was present, so 1 g of di-tert-butyldicarbonate was added.

The mixture was filtered and the filtrate was concentrated to dryness. The residue was dissolved in H$_2$O and washed with Et$_2$O and the aqueous layer was adjusted to pH 4 with HOAc. The acidic solution was wasned with EtOAc. The aqueous layer containing the product was treated with anion exchange resin (AG-3 acetate, BioRad) and concentrated to dryness.

The crude product was passed through a hydrophobic chromatography column (Amberlite XAD-2, Rohm & Haas) by elution with a gradient from H$_2$O to 25% EtOH. The fractions containing product were pooled to yield 2.7 g of N$^\alpha$-Boc-N$^G$,N$^{G'}$-ethano-D-homoarginine, $[\alpha]_D^{25}$ −19.7° (c 0.1, MeOH).

In a similar fashion, by substituting:
S-methyl-dimethyl-iso-thiourea-HI,
S-methyl-diethyl-iso-thiourea-HI,
S-methyl-dipropyl-iso-thiourea-HI,
S-methyl-dibutyl-iso-thiourea-HI,
S-methyl-dipentyl-iso-thiourea-HI,
S-methyl-dihexyl-iso-thiourea-HI,
S-methyl-diheptyl-iso-thiourea-HI, and
S-methyl-dinonyl-iso-thiourea-HI or their corresponding free bases for 2-methylthio-2-imidazoline-HI, there are obtained:
N$^\alpha$-Boc-N,N'-guanidino-dimethyl-D-homoarginine, $[\alpha]_D^{25}$ 19.5° (C 0.4, MeOH),
N$^\alpha$-Boc-N,N'-guanidino-diethyl-D-homoarginine, $[\alpha]_D^{25}$ 13.4° (C 0.6, MeOH),
N$^\alpha$-Boc-N,N'-guanidino-di-n-propyl-D-homoarginine, $[\alpha]_D^{25}$ 11.3° (C 0.4, MeOH),
N$^\alpha$-Boc-N,N'-guanidino-di-cyclohexyl-D-homoarginine, $[\alpha]_D^{25}$ 0.7° (C 0.7, MeOH),
N$^\alpha$-Boc-N,N'-guanidino-di-n-butyl-D-homoarginine, $[\alpha]_D^{25}$ 11.1° (C ,1MeOH),
N$^\alpha$-Boc-N,N'-guanidino-dipentyl-D-homoarginine,
N$^\alpha$-Boc-N,N'-guanidino-di-n-hexyl-D-homoarginine,
N$^\alpha$-Boc-N,N'-guanidino-diheptyl-D-homoarginine,
N$^\alpha$-Boc-N,N'-guanidino-dinonyl-D-homoarginine, and
N$^\alpha$-Boc-N,N'-guanidino-diisopropyl-D-homoarginine.

PREPARATION C

A mixture of 3.0 g benzyl N$^\alpha$-benzyloxycarbonyl-N$^{G,NG'}$-diethyl-D-homoargininate toluenesulfonate salt and 0.5 g of 10% Pd/C catalyst in 100 ml EtOH was treated with H gas at room temperature and pressure for 3 hours. The solution was filtered through Celite, wasned with EtOH and concentrated to give 2.1 g of N,N'-guanidino-diethyl-D-homoarginine toluenesulfonate salt as a white foam, $[\alpha]_D^{25}$ 6.0° (C 1.0, MeOH), In a similar fashion, using the corresponding protected amino acids from preparation A, there were obtained:
N,N'-guanidino-dimethyl-D-homoarginine,
N,N'-guanidino-dicyclohexyl-D-homoarginine, $[\alpha]_D^{25}$ 7.6° (C 0.1, MeOH);
N,N'-guanidino-di-n-propyl-D-homoarginine, $[\alpha]_D^{25}$ 7.1° (C 0.4, MeOH);
N,N'-guanidino-n-butyl-D-homoarginine, $[\alpha]_D^{25}$ 6.3° (C 0.5, MeOH);
N,N'-guanidino-i-butyl-D-homoarginine;
N,N'-guanidino-n-pentyl-D-homoarginine;
N,N'-guanidino-di-phenyl-D-homoarginine, $[\alpha]_D^{25}$ 11.7° (C 0.5, MeOH);
N,N'-guanidino-di-n-hexyl-D-homoarginine, $[\alpha]_D^{25}$ 8.3° (C 0.3 MeOH);
N,N'-guanidino-di-i-propyl-D-homoarginine, $[\alpha]_D^{25}$ 3.52° (C 0.3, MeOH); and
N-guanidino-(3-dimethylaminopropyl)-N'-guanidinoyl-D-homoarginine as their toluenesulfonate salts.

Similarly, utilizing the arginine derivatives, there will be obtained the corresponding dialkylarginine derivatives, for example:
N,N'-guanidino-dimethyl-D-arginine;

N,N'-guanidino-diisopropyl-D-arginine, $[\alpha]_D^{25}$ 10.5° (C0.4, MeOH);

N,N'-guanidino-diethyl-D-arginine, and the like.

PREPARATION D

This Preparation illustrates the preparation of $N^\alpha$-t-butyloxy carbonyl derivatives of N,N'-guanidino-disubstituted-D-homoarginines from their toluenesulfonate precursors.

A mixture of N,N'-guanidino-diisopropyl-D-homoargininate toluenesulfonate (3.25 g) and 100 mg of 10% Pd/C in 50 ml of glacial acetic acid is treated with hydrogen gas at atmospheric pressure for 4 hours. The catalyst is filtered on celite and the filtrate is concentrated to a solid, N,N'-guanidino-diisopropyl-D-homoarginine toluenesulfonate. A solution of this compound (2.13 g) in 60 ml of 50% dioxane/water is treated with 10 ml of 1N sodium hydroxide and 0.4 g of magnesium oxide. This mixture is then treated with 1.1 g of di-t-butyldicarbonate and stirred at room temperature for 2 hours. The magnesium salt is filtered and the filtrate is concentrated under vacuum. The basic solution is washed with ethanol, then brought to pH 2.5 with sodium sulfate. The acidic aqueous solution is extracted with ethyl acetate which is dried over magnesium sulfate. The drying agent is filtered and the filtrate is concentrated. Crystallization from ethyl acetate/hexane affords $N^\alpha$-t-butyloxycarbonyl-N,N'-guanidino-diisopropyl-D-homoarginine toluenesulfonate, $[\alpha]_D^{25}$ 1.2° (C 0.7, MeOH).

Proceeding in a similiar manner, but substituting the appropriate toluenesulfonate precursor from Preparation D, other $N^\alpha$-t-butyloxycarbonyl-N,N'-guanidino-disubstituted-D-homoarginine or D-arginine compounds may be prepared.

PREPARATION E $N^\alpha$-t-butyloxycarbonyl-3-(4'-(1'-propylpiperidyl))-D-alanine A 4.6 g portion of sodium metal was added to 400 ml of absolute ethanol and heated. To the resultant solution of sodium ethoxide was added 21.7 g of diethyl acetamidomalonate and 16.4 g of 4-picolyl chloride hydrochloride (Aldrich Chem. Co.). The reaction mixture was heated to 100° C. for 4 hours, cooled, filtered and concentrated in vacuo. Tne mixture was loaded on a silica gel column in methylene chloride/methanol (19:1) and eluted with tne same mixture. The product was located as a fast running UV positive spot by TLC on silica gel in methylene chloride/methanol (19:1). Combined fractions were concentrated to provide the product.

The product from the foregoing paragraph was dissolved in 200 ml of ethanol and treated with a solution of 2.72 g of sodium hydroxide in 40 ml of water at 50° C. for 6 hours. The solution was acidified with 12 ml of 6N HCl, concentrated to dryness and taken up in 200 ml of dioxane. The suspension was filtered and the filtrate heated at reflux for 2 hours. The solution was cooled and concentrated to dryness to yield ethyl $N^\alpha$-acetyl-3-(4-pyridyl)-D,L-alanine as a white solid.

A portion of this N-acetyl ester was resolved by treatment with 200 ml of the enzyme subtilisin Carlsberg (Sigma Chem. Co., protease VIII) in a mixture of 300 ml of dimetnyl sulfoxide and 400 ml of 0.01M KCl (pH 7.2). The pH was maintained by addition of 1N NaOH on a pH stat. After a 6 hour period, the resolution was complete. The solution was diluted with 400 ml of water and extracted with 4×750 ml of ethyl acetate. The organic layers were combined and dried over magnesium sulfate and concentrated to yield ethyl $N^\alpha$-acetyl-3-(4-pyridyl)-D-alaninate as an oil.

The oil was reacted with 1.22 g of n-propyl bromide in 50 ml of ethanol after which the solution was concentrated to dryness to yield ethyl $N^\alpha$-acetyl-3-(1-propylpyridinium-4-yl)-alininate bromide as a white hygroscopic solid.

This white solid was dissolved in 200 ml of ethanol and was reduced under an atmosphere of hydrogen gas using 100 mg of 10% Pd/C as a catalyst. After an 18 hour reduction period, the catalyst was filtered out and the solution concentrated to yield ethyl $N^\alpha$-acetyl-3-(4'-(1'-propylpiperidyl))-D-alininate as a tan solid. The free acid was prepared by refluxing the ethyl ester in 100 ml of 6N HCl for 4 hours to yield 3-(4'-(1'-propylpiperidyl))-D-alanine as a white solid.

The free acid was dissolved in 100 ml of dioxane/water (1:1) and treated with 2 g of di-t-butyldicarbonate. The pH was maintained at 9 by addition of 1N NaOH on a pH stat. After 2 hours the reaction mixture was concentrated in vacuo, washed with 100 ml of ethyl ether and the aqueous laye was loaded on an Amberlite XAD-2 hydrophobic resin. The column was eluted with 250 ml of water followed by 250 ml of 50% ethanol/ater. The ethanol eluate was pooled and concentrated to dryness to yield $N^\alpha$-t-butyloxycarbonyl-3-(4'-(1'-propylpiperidyl))-D-alanine as a white solid.

Proceeding in similiar manner, but substituting 3-picolyl chloride hydrochloride for 4-picolyl chloride hydrochloride, there is prepared $N^\alpha$-t-butyloxycarbonyl-3-(3'-(1'-propylpiperidyl))-D-alanine.

EXAMPLE 1

In the reaction vessel of a Beckman 990 Peptide Synthesizer was placed 0.8 g. (0.8 mmol.) of benzhydrylamino-polystyrene-divinylbenzene resin (Lab Systems, Inc.) as described by Rivaille, supra. Amino acids were added sequentially to this resin by means of a synthesis program, as follows:

| Step | | | |
|---|---|---|---|
| 1 | $CH_2Cl_2$ wash | 1 time | 1.5 min |
| 2 | 50% $CF_3CO_2H/CH_2Cl_2$—deprotection | 1 time | 1.5 min |
| 3 | 50% $CF_3CO_2H/CH_2Cl_2$—deprotection | 1 time | 30 min |
| 4 | $CH_2Cl_2$ wash | 3 times | 1.5 min |
| 5 | 10% triethylamine/$CH_2Cl_2$ | 2 times | 1.5 min |
| 6 | $CH_2Cl_2$ wash | 3 times | 1.5 min |
| 7 | $N^\alpha$—Boc—amino acid solution | 1 time | add |
| 8 | N,N'—dicyclohexylcarbodiimide solution | 1 time | add |
| 9 | $CH_2Cl_2$ rinse and hold-coupling | 1 time | coupling reaction 2 hr |
| 10 | $CH_2Cl_2$—rinse add | 1 time | 1.5 min |
| 11 | $CH_2Cl_2$ wash | 3 times | 1.5 min |
| 12 | ethanol wash | 3 times | 1.5 min |
| 13 | $CH_2Cl_2$ wash | 3 times | 1.5 min |

Steps 1–13 complete a coupling cycle for one amino acid and completeness of the reaction is checked by the ninhydrin method of E. Kaiser, et al., *Anal. Biochem.*, 34, 595 (1970).

The resin was coupled sequentially with a 2.5 molar excess of each protected amino acid and DCC. Thus, the resin was treated during successive coupling cycles with 0.433 g. Boc-Gly-OH,
0.432 g. Boc-Pro-OH,
0.857 g. Boc-Arg(Tosyl)-OH,
0.562 g. Boc-Leu-OH.½ H$_2$O,
0.52 g. N$^\alpha$-Boc-N$^G$,N$^{G'}$-diethyl-homoarginine.HOAc.
0.724 g N-Boc-O-2,6-dichlorobenzyltyrosine,
0.59 g. Boc-Ser(Benzyl)-OH,
0.608 g. Boc-Trp-OH,
0.654 g. Boc-His(Tosyl)-OH, and
0.524 g. pyroglutamic acid.

The resin was removed from the reaction vessel, washed with CH$_2$Cl$_2$, and dried in vacuo to yield 2.2 g. of protected polypeptide resin.

The polypeptide product was simultaneously removed from the resin and completely deprotected by treatment with anhydrous liquid HF. A mixture of 2.0 g. of protected polypeptide resin and 2 mL. of anisole (scavenger) in a Kel-F reaction vessel was treated with 20 mL. of redistilled (from CoF$_3$) anhydrous liquid HF at 0° C. for 30 minutes. The HF was evaporated under vacuum and the residue of (pyro)-Glu-His-Trp-Ser-Tyr-D-Deh-Leu-Arg-Pro-Gly-NH$_2$, as its HF salt, was washed witn ether. Tne residue was then extracted with glacial acetic acid. The acetic acid extract was lyophilized to yield 0.8 g. of crude material as the HF salt. This material was converted to the acetate salt by passage through a column of weakly basic anion exchange resin (Bio Rad Ag3, acetate form). Lyphilization of the eluate yielded the crude material as the acetate salt.

Final purification was achieved by preparative high performance liquid chromatography of a 200 mg sample on a 2.5×100 cm column of 40–50 μm octadecylsilylated silica (Merck, Licroprep C-18). The eluent was 70% 0.06 M HN$_4$OAc/30% CH$_3$CN at pH 7. In two runs, a total of 400 mg of crude material was purified. After 3 lyophilizations from water, 100 mg of pure pGlu-His-Trp-Ser-Tyr-D-Deh-Leu-Arg-Pro-GlyNH$_2$ maybe obtained as its acetic acid addition salt.

EXAMPLE 2

For the synthesis of analogues with a C-terminal Pro-NH-CH$_2$CH$_3$, a synthesis program identical to that described in Example 1 was used. The Beckman 990 Synthesizer reaction vessel was loaded with 4.62 g. of Boc-Pro-O-Resin, prepared by the reaction of equimolar ratios of the dry cesium salt of Boc-Pro-OH with chloromethyl-polystyrene/1% divinylbenzene (Lab Systems, Inc.). The quantity of Boc-Pro-O-Resin taken contained 4.0 mmol. of proline.

The resin was coupled sequentially with an approximately 2.5 molar excess of each protected amino acid and DCC. The ratio used for the more expensive or unnatural protected amino acids was lower. Thus, resin was reacted during successive coupling cycles with
4.28 g. Boc-Arg(Tosyl)-OH,
2.49 g. Boc-Leu-OH.½H O$_2$, At this point in the synthesis the protected polypeptide resin was removed, dried in vacuo and 0.825 g (0.5 mmol) of the protected tripeptide-resin was carried through to completion by sequential reaction with:
0.4 g. Boc-D-Deh-OH.HOAc and 0.155 g HBT;
0.53 g Boc-O-2,6-dichlorobenzyl-L-Tyrosine; and 0.19 g HBT;
0.37 g Boc-Ser(benzyl)-OH;
0.38 g. Boc-Trp-OH;
0.512 g. Boc-His(Tosyl)-OH; and
0.162 g. pyroglutamic acid.

The resin was removed from the reaction vessel, washed with CH$_2$Cl$_2$, and dried in vacuo to yield 1.32 g. of protected polypeptide resin.

The protected polypeptide was cleaved from the resin by aminolysis with 35 mL. of ethylamine for 18 hours at 0° C. The ethylamine was allowed to evaporate and the resin was extracted with methanol/dimethylformamide. The solvents were evaporated to yield 0.53 g. of pyro-Glu-His(Tosyl)-Trp-Ser(Benzyl)-Tyr(2,6-dichlorobenzyl-D-Deh-Leu-Arg(Tosyl)-Pro-NH-CH$_2$CH$_3$.

The crude polypeptide was deprotected by treatment with a mixture of 3.2 mL. anisole and 25 mL. redistilled (from CoF$_3$) anhydrous liquid HF at 0° C. for 1 hr in a Kel-F reaction vessel. The HF was evaporated under vacuum and the residue was washed with ether. The residue was dissolved in acetic acid and evaporated to near dryness, dissolved in 50 ml of H$_2$O and converted to the acetate salt by passage on a short weakly basic anion exchange resin (BioRad Ag3) in its acetate form. The eluate was lyophilized to yield 0.42 g. of crude (pyro)-Glu-His-Trp-Ser-Tyr-D-Deh-Leu-Arg-Pro-NH-CH$_2$CH$_3$ as its acetic acid addition salt.

Final purification was achieved by preparative high performance liquid chromatography of a 210 mg. sample on a 2.5×100 cm. column of 40–50 μm octadecylsilylated silica (Merck, Lichroprep C$_{18}$). The eluant was 8% 0.06 M NH$_4$OAc/36% acetonitrile at pH 7. In two runs a total of 420 mg. of crude material was purified. After three lyophilizations from water, 129 mg. of pure pyroglutamyl-histidyl-tryptophyl-seryl-tyrosyl-D-Deh-leucyl-arginyl-proline ethylamide was obtained as its acetic acid addition salt, m.p. 165°–170° C., $[\alpha]_D^{25}$ 29.2° (C 1, HOAc).

Repeating the above cleavage, substituting a stoichiometric amount of:
n-butylamine,
cyclopropylamine,
cyclohexylamine,
trifluoromethylamine,
pentafluoroethylamine, and
2,2,2-trifluoroethylamine
for ethylamine there are obtained the corresponding
n-butylamide,
cyclopropylamide,
cyclohexylamide,
trifluoromethylamide,
pentafluoroethylamide, and
2,2,2-trifluoroethylamide
of the aforementioned nonapeptide.

EXAMPLE 3

Compounds of Formula I wherein Z is

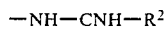

may be prepared by classical solution synthesis.

For example, the following approach may be used wherein "azaGlyNH$_2$" is

```
(pyro)Glu—His—Trp—Ser—          Cbz—Leu—Arg—azaGlyNH₂
        Tyr—OMe                            |
                                           NO₂
                                    | (a) H₂/Pd/C
                                    | (b) Boc—D—Deh—OH
                                    |     (DCC/HBT)
                                    ▼
                        Boc—D—Deh—Leu—Arg—Pro—azaGly—NH₂
                                    H⁺

|                                 |
          ▼                                 ▼
  (pyro)Glu—His—Trp—
       Ser—Tyr—N₃
                                    | HCl/EtOAC
                                    ▼
                     H—D—Deh—Leu—Arg—Pro—azaGly—NH₂
          |_____|
                      ▼
            (pyro)Glu—His—Trp—Ser—Tyr—D—Deh—
                   Leu—Arg—Pro—azaGly—NH₂
``` as the free peptide or salt.

The coupling of the individual fragments may proceed by the acyl azide method (J. Honzel, et al, *Coll. Czech. Chem. Comm*, 26, 2333 (1971)), by DCC/HBT coupling or other razation free fragment coupling techniques. Compounds (1) and (2) are known (M. Fujino, et al, *Biochem. Biophys. Res. Comm.*, 57, 1248 (1974) and A. S. Dutta, et al., *J. Chem. Soc. Perkin I*, 1979, 379, respectively). Compound (3) is prepared from (2) by removal of the Cbz and nitro groups by hydrogenolysis, followed by coupling with N-Boc-D-Deh-OH using DCC/HBT or other coupling agent known in the art. See Dutta, et al, supra, for a similar LH-RH analogue synthesis.

Alternatively, and preferably, this analog may be prepared by coupling of the corresponding nonapeptide acid (i.e., pGlu-His-Trp-Ser-Tyr-D-Deh-Leu-Arg-Pro-OH) with semicarbazide.HCl in the presence of DCC/HBT. The Desired nonapeptide acid is prepared by HF cleavage of the protected nonapeptide-O-resin described in Example 2.

Similarly, utilizing other amino acids in place of $N^\alpha$-Boc-D-Deh-OH, other compounds of Formula I may be prepared, e.g.
(pyro)Glu-His-Trp-Ser-Tyr-D-Dmh-N-methyl-Leu-Arg-Pro-azaGlyNH₂;
(pyro)Glu-His-Trp-Ser-Tyr-D-Eth-Leu-Arg-Pro-azaGlyNH₂; and
(pyro)Glu-His-Trp-Ser-Tyr-D-Dbh-Leu-Arg-Pro-azaGlyNH₂.

Also, in the preparation of compound (2), use of azaGly-NH-lower alkyl in place of aza-Gly-NH₂ affords the corresponding peptide with an azaGly-NH-lower alkyl terminus, e.g.:
(pyro)Glu-His-Trp-Ser-Tyr-D-Deh-Leu-Arg-Pro-azaGly-NHEt;
(pyro)Glu-His-Trp-Ser-Tyr-D-Deh-N-methyl-Leu-Arg-Pro-azaGly-NHEt; and
(pyro)Glu-His-Trp-Ser-Tyr-D-Har-Leu-Arg-Pro-azaGly-NHEt.

EXAMPLE 4

Repeating the procedure of Example 1 and utilizing either a D-amino acid or a D,L amino acid at position 6 (in the latter case, separating the diastereomeric peptides during chromatography), substituting the appropriate amino acids in the solid phase synthesis sequence, there may be obtained the following decapeptides which are isolated and characterized as tneir acetic acid addition salts:
(pyro)Glu-His-Trp-Ser-Tyr-D-Dmh-Leu-Arg-Pro-Gly-NH₂;
(pyro)Glu-His-Trp-Ser-Tyr-D-Dph-Leu-Arg-Pro-Gly-NH₂;
(pyro)Glu-His-Trp-Ser-Tyr-D-Eth-Leu-Arg-Pro-Gly-NH₂;
(pyro)Glu-His-Trp-Ser-Tyr-D-Deh-N-MeLeu-Arg-Pro-Gly-NH₂;
(pyro)Glu-His-Trp-Ser-Tyr-D-Deh-Leu-Gln-Pro-Gly-NH₂;
(pyro)Glu-His-Trp-Ser-Tyr-D-Deh-Trp-Leu-Pro-Gly-NH₂;
(pyro)Glu-His-Trp-Ser-Tyr-D-Dph-N-MeLeu-Arg-Pro-Gly-NH₂; and
(pyro)Glu-His-Nal(2)-Ser-Tyr-D-Deh-N-MeLeu-Arg-Pro-Gly-NH₂.

EXAMPLE 5

Repeating the procedure of Example 2 and utilizing either a D-amino acid or a D,L amino acid at position 6 (in the latter case, separating the diastereomeric peptides during chromatography), substituting the appropriate amino acids in the solid phase synthesis sequence, there may be obtained the following nonapeptides whicn are isolated and characterized as their acetic acid addition salts:
(pyro)Glu-His-Trp-Ser-Tyr-D-Dmh-Leu-Arg-Pro-NH-Et;
(pyro)Glu-His-Trp-Ser-Tyr-D-Dph-Leu-Arg-Pro-NH-Et;
(pyro)Glu-His-Trp-Ser-Tyr-D-Deh-Leu-Gln-Pro-NH-Et;
(pyro)Glu-His-Trp-Ser-Tyr-D-Deh-Trp-Leu-Pro-NH-Et;
(pyro)Glu-His-Trp-Ser-Tyr-D-Dhh-Leu-Arg-Pro-NH-Et; $[\alpha]_D^{25}$ 27.1° (C 0.6, HOAc).

(pyro)Glu-His-Trp-Ser-Tyr-D-Eth-Leu-Arg-Pro-NH-Et; $[\alpha]_D^{25}$ 27.8° (C 0.3, HOAc).

(Pyro)Glu-His-Trp-Ser-Tyr-D-Deh-N-MeLeu-Arg-Pro-NH-Et; and (Pyro)Glu-His-Nal(2)-Ser-Tyr-D-Deh-N-MeLeu-Arg-Pro-NH-Et.

EXAMPLE 6

A. A solution of 0.1 g of the hydrogen fluoride salt of (pyro)Glu-His-Trp-Ser-Tyr-D-Deh-Leu-Arg-Pro-NHEt (See Example 1) is dissolved in 50 mL of water and passed through a column of 50 g Dowex 3 anion exchange resin which had previously been equilibrated with acetic acid and washed with deionized water. The column is eluted with deionized water and the effluent is lyophilized to yield the corresponding acetic acid salt of (pyro)Glu-His-Trp-Ser-Tyr-D-Eth-Leu-Arg-Pro-NH-EtH, $[\alpha]_D^{25}$ 29.2° (C 1, HOAc).

Repeating the above, substituting other acids for acetic acid during the equilibration of the resin, there may be obtained, for example, the corresponding salts with hydrochloric acid, nydrobromic acid, sulfuric acid, phosphoric acid, nitric acid, benzoic acid, and the like.

Similarly there may be prepared the acid addition salts of other compounds of Formula I.

B. In the case of salts of low water solubility, tnese may be prepared by precipitation from water utilizing the desired acid. For example:

Zinc tannate salt—a solution of 10 mg of (pyro)Glu-His-Trp-Ser-Tyr-D-Den-Leu-Arg-Pro-NH-Et acetic acid salt in 0.1 mL of water was treated with a solution of 8 mg of tannic acid in 0.08 mL of 0.25 M NaOH. A solution of 5 mg of $ZnSO_4$ heptahydrate in 0.1 mL of water was immediately added to the solution of the LH-RH analogue.

The resultant suspension was diluted with 1 mL water and the precipitate was centrifuged. The supernatant was decanted and the residue was washed twice with 1 mL portions of water by centrifugation of the precipitate and decantation of the supernatant. The precipitate was dried in vacuo to yield 15 mg of the mixed zinc tannate salt of the above named LH-RH analogue.

Pamoate salt—to a solution of 50 mg (pyro)Glu-His-Trp-Ser-Tyr-D-Deh-Leu-Arg-Pro-NHEt acetic acid salt in a mixture of 1.6 mL of ethanol and 0.1 mL of 0.25 M NaOH was added solution of 11 mg of pamoic acid in 0.3 mL of 0.25 M NaOH. The solvents were removed at reduced pressure and the residue was suspended in 2 mL of water, centrifuged, and the supernatant was decanted. The precipitate was washed with 1.5 mL $H_2O$, centrifuged, and the supernatant was decanted. The precipitate was dried in vacuo to yield 54 mg of the pamoate salt of the above named LH-RH analogue.

In a similar manner other salts of low water solubility may be prepared.

C. Preparation of acid addition salt from free peptide.

To a solution of 50 mg of (pyro)Glu-His-Trp-Ser-Tyr-D-Deh-Leu-Arg-Pro-NHEt as the free base is added 30 mL of 1N acetic acid. The resulting solution is lyophilized to yield 50 mg. of the acetic acid salt of the above-named LH-RH analogue.

Similarly, replacing acetic acid with other acids (in stoichiometrically equivalent amounts relative to peptide) there was obtained other acid additon salts of compounds of Formula (I), for example, the salts with hydrochloric acid, hydrobromic acid, sulfuric acid, phosphoric acid, nitric acid.

D. Preparation of salt with metal cation, e.g., zinc salt:

To a solution of 50 mg (pyro)Glu-His-Trp-Ser-Tyr-D-Deh-Leu-Arg-Pro-NH-Et acetic acid salt in a mixture of 0.4 mL of 0.25 M NaOH, 0.3 mL water, and 1 mL ethanol was added a solution of 15 mg of $ZnSO_4$ heptahydrate in 0.2 mL of water. The precipitate was centrifuged and the supernatant was decanted. The precipitate was washed with 1 mL of water by centrifugation and decantation of the supernatant. The precipitate was dried in vacuo to yield 48 mg of the zinc salt of the above named LH-RH analogue.

In a similar manner salts with other multivalent cations e.g. calcium, bismuth, barium, magnesium, aluminum, copper, cobalt, nickel, cadmium and the like, may be prepared.

EXAMPLE 7

A solution of 50 mg of (pyro)Glu-His-Trp-Ser-Tyr-D-Deh-Leu-Arg-Pro-NHEt acetic acid salt in 25 ml of water is passed through a 50 g column of Dowex 1 (strongly basic, quaternary ammonium anion exchange resin) which had been equilibrated with NaOH solution to make the counter ion hydroxide. Tne column is eluted with 150 ml of water and the eluant is lyophilized to yield 45 mg of the corresponding polypeptide as the free base.

Similarly other acid additions salts of compounds of Formula (I), e.g. those mentioned in Example 6, may be converted to the corresponding free bases.

EXAMPLE 8

The following are typical pharmaceutical compositions containing, as active ingredient, an LH-RH analogue of the present invention, for example (pyro)Glu-His-Trp-Ser-Tyr-D-Deh-Leu-Arg-Pro-NHEt, by itself or as a pharmaceutically acceptable salt, e.g. the acetic acid addition salt, the zinc salt, the zinc tannate salt, etc.

A. Tablet formulations for buccal (e.g. sublingual) administration:

| | | |
|---|---|---|
| 1. | LH—RH Analogue | 50.0 *g |
| | Compressible Sugar, USP | 96.0 mg |
| | Calcium Stearate | 4.0 mg |
| 2. | LH—RH Analogue | 30.0 *g |
| | Compressible Sugar, USP | 98.5 mg |
| | Magnesium Stearate | 1.5 mg |
| 3. | LH—RH Analogue | 25.0 *g |
| | Mannitol, USP | 88.5 mg |
| | Magnesium Stearate, USP | 1.5 mg |
| | Pregelatinized Starch, USP | 10.0 mg |
| 4. | LH—RH Analogue | 200.0 *g |
| | Lactose, USP | 83.3 mg |
| | Pregelatinized Starch, USP | 15.0 mg |
| | Magnesium Stearate, USP | 1.5 mg |

Method of Manufacture a. LH-RH Analogue is dissolved in water, a sufficient quantity to form a wet granulation when mixed with the sugar portion of the excipients. After complete mixing, the granulation is dried in a tray or fluid-bed dryer. The dry granulation is then screened to break up any large aggregates and then mixed with the remaining components. The granulation is then compressed on a standard tabletting machine to the specific tablet weight.

b. In this manufacturing method, all formulations would include 0.01% gelatin, USP. The gelatin would be first dissolved in the aqueous granulation solvent followed by the LH-RH analog. The remaining steps are as in (a) above.

Formulation 4 could also be used as a tablet for oral administration.

B. Long Acting intramuscular injectable formulation.

| 1. Long Acting I.M. Injectable - Sesame Oil Gel | |
|---|---|
| LH—RH Analogue | 1.0 mg |
| Aluminum monostearate, USP | 20.0 mg |
| Sesame oil q.s. ad | 1.0 ml |

The aluminum monostearate is combined with the sesame oil and heated to 125° C. with stirring until a clear yellow solution forms. This mixture is then autoclaved for sterility and allowed to cool. The LH-RH analogue is tnen added aseptically with trituration. Particularly preferred LH-RH analogues are salts of low solubility, e.g. zinc salts, zinc tannate salts, pamoate salts, and the like. These exhibit exceptionally long duration of activity.

| 2. Long Acting I.M. Injectable - Biodegradable Polymer Microspheres | |
|---|---|
| LH—RH Analogue | 1% |
| 25/75 glycolide/lactide copolymer (0.5 intrinsic viscosity) | 99% |

Microspheres of the above formulation suspended in:

| | |
|---|---|
| Dextrose | 5.0% |
| CMC, sodium | 0.5% |
| Benzyl alcohol | 0.9% |
| Tween 80 | 0.1% |
| Water, purified q.s. | 100.0% |

25 mg of microcapsules would be suspended in 1.0 ml of vehicle.

C. Aqueous Solution for Intramuscular Injection

| | |
|---|---|
| LH—RH Analogue | 25 mg |
| Gelatin, nonantigenic | 5 mg |
| Water for injection q.s. ad | 100 ml |

Dissolve gelatin and LH-RH analogue in water for injection, then sterile filter solution.

D. Aqueous Solution for Nasal Administration

| | |
|---|---|
| LH—RH Analogue | 250 mg |
| Dextrose | 5 gm |
| Benzyl alcohol | 0.9 gm |
| Na glycholate | 0.5 gm |
| Water, purified q.s. ad | 100 ml |

Dissolve LH-RH analogue, dextrose, benzyl alcohol in purified water and q.s. to volume.

E. Formulation for Rectal Administration Suppository Vehicle for Rectal Administration

| | |
|---|---|
| LH—RH Analogue | 500 μg |
| Witepsol H15 | 20.0 gm |

The LH-RH analogue is combined with the molten Witepsol H15, mixed well and poured into 2 gm molds.

What we claim is:

1. A compound of the formula (pyro)Glu-His-A-Ser-B-C-D-Ed-Pro-F    (I)

and the pharmaceutically acceptable salts thereof wherein:

A is tryptophyl, phenylalanyl, 3-(1-naphthyl)-L-alanyl or 3-(2-naphthyl)-L-alanine;

B is tyrosyl, phenylalanyl or 3-(1-pentafluorophenyl)-L-alanyl, ;

C is an amino acyl residue selected from the group consisting of the radicals represented by the following structural formulas:

(a)

wherein n is 1 to 5;

$R_1$ is alkyl of 1 to 12 carbon atoms, $-NRR_3$ wherein R is hydrogen or alkyl of 1 to 4 carbon atoms, $R_3$ is fluoroalkyl, alkyl of 1 to 12 carbon atoms, cycloalkyl, phenyl, benzyl, $-(CH_2)_n$-morpholino or $-(CH_2)_nN(R_4)_2$ wherein n is 1 to 5 and $R_4$ is lower alkyl;

$R_2$ is hydrogen or $R_3$; or $R_1$ and $R_2$ comprise a ring represented by the following structural formulas:

IIA

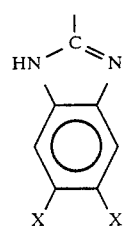

IIB

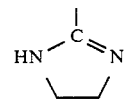

IIC

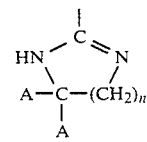

IID wherein n is 1 to 7; A is hydrogen, alkyl of 1 to 6 carbon atoms or cycloalkyl; and X is halo or A or (b)

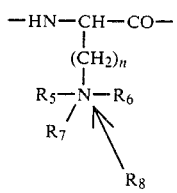

(III)

wherein $R_5$ is alkyl of 1 to 6 carbon atoms, benzyl, phenylethyl, cyclohexyl, cyclopentyl; and $R_6$, $R_7$ and $R_8$ are hydrogen or alkyl of 1 to 4 carbon atoms; and n is the integer 2–5; or (c) a substituent of the formula

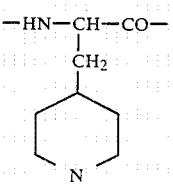

(IV)

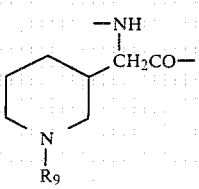

(V)

wherein $R_9$ is hydrogen, alkyl of 1 to 12 carbon atoms, phenyl or phenylloweralkyl;

E is arginyl or leucyl: and

D is leucyl, isoleucyl, nor-leucyl or N-methylleucyl;

F is glycinamide or $-NH-R^1$, wherein $R^1$ is lower alkyl, cycloalkyl, fluoro lower alkyl or $-N-H-CO-NH-R^2$ wherein $R^2$ is hydrogen or lower alkyl.

2. The compound of claim 1 wherein

C is an amino acyl residue selected from the group consisting of the radicals represented by the following structrual formulas:

(a)

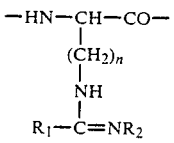

(II)

wherein n is 4;

$R_1$ is $-NRR_3$ wherein R is hydrogen, $R_3$ is hydrogen, alkyl of 1 to 6 carbon atoms, cycloalkyl or fluoroalkyl;

$R_2$ is alkyl of 1 to 12 carbon atoms, cycloalkyl or fluoroalkyl; or $R_1$ and $R_2$ comprise a ring represented by the following structural formula:

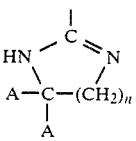

IID wherein n is 1; and A is hydrogen.

3. The compound of claim 2 wherein C is an amino acyl residue wherein R is hydrogen and $R_3$ is methyl, ethyl, or hexyl;

$R_2$ is the same as $R_3$ or $R_1$ and $R_2$ together form the ring of formula IID.

4. The compound of claim 3 which is (pyro)Glu-L-His-L-Trp-L-Ser-L-Tyr-D-Eth-L-Leu-L-Arg-L-Pro-NHEt and its pharmaceutically acceptable salts.

5. The compound of claim 3 which is (pyro)Glu-L-His-L-Trp-L-Ser-L-Tyr-D-Deh-L-Leu-L-Arg-L-Pro-NHEt and its pharmaceutically acceptable salts.

6. The compound of claim 3 which is (pyro)Glu-L-His-L-Trp-L-Ser-L-Tyr-D-Dhh-L-Leu-L-Arg-L-Pro-NHEt and its pharmaceutically acceptable salts.

7. The compound of claim 3 which is (pyro)Glu-L-His-L-Trp-L-Ser -L-Tyr-D-Deh-L-MeLeu-L-Arg-L-Pro-NHET and its pharmaceutically acceptable salts.

8. The compound of claim 3 which is (pyro)Glu-L-His-L-Nal(2) -L-Ser-L-Tyr-D-Deh-L-Leu-L-Arg-L-Pro-NHEt and its pharmaceutically acceptable salts.

9. The compound of claim 3 which is (pyro)Glu-L-His-L-Trp-L-Ser-L-Tyr-D-Deh-L-Leu-L-Arg-L-Pro-GlyNH$_2$ and its pharmaceutically acceptable salts.

10. The compound of claim 3 which is (pyro)Glu-L-His-L-Trp-L-Ser-L-Tyr-D-Den-L-MeLeu-L-Arg-L-Pro-GlyNH$_2$ and its pharmaceutically acceptable salts.

11. The compound of claim 3 which is (pyro)Glu-L-His-L-Nal(2) -L-Ser-L-Tyr-D-Deh-L-MeLeu-L-Arg-L-Pro-GlyNH$_2$ and its pharmaceutically acceptable salts.

12. The compound of claim 1 wherein A is Trp, B is Tyr, D is Leu and E is Gln.

13. The compound of claim 12 wherein D is D-Deh and F is GlyNH$_2$ which is (pyro)Glu-L-His-L-Trp-L-Ser-L-Tyr-D-Den-L-Leu-L-Gln-L-Pro-GlyNH$_2$ and its pharmaceutically acceptable salts.

14. The compound of claim 12 wherein D is D-Deh and F is NHEt which is (pyro)Glu-L-His-L-Trp-L-Ser-L-Tyr-D-Deh-L-Leu-L-Gln-L-Pro-NHEt and its pharmaceutically acceptable salts.

15. The compound of claim 1 wherein A is Trp, B is Tyr, D is Trp and E is Leu.

16. Tne compound of claim 15 wherein C is Deh and F is GlyNH$_2$ which is (pyro)Glu-L-His-L-Trp-L-Ser-L-Tyr-D-Deh-L-Trp-L-Leu-L-Pro-GlyNH$_2$ and the pharmaceutically acceptable salts thereof.

17. The compound of claim 15 wherein C is Deh and F is NHEt which is (pyro)Glu-L-His-L-Trp-L-Ser-L-Tyr-D-Deh-L-Trp-L-Leu-L-Pro-NHEt and the pharmaceutically acceptable salts thereof.

18. A method of inhibiting ovulation in a female mammalian subject which method comprises administering to said subject an effective amount of a compound of claim 1.

19. A method of treating benign prostatic hypertrophy in a male mammalian subject which method comprises administering to said subject an effective amount of a compound of the formula of claim 1 either alone or in admixture with a pnarmaceutically acceptable excipient.

20. A metnod of treating fibrocystic breast disease in a mammalian subject wnich method comprises administering to said subject an effective amount of a compound of tne formula of claim 1 or a pharmaceutical composition containing same.

21. A method of lowering, blocking or abolishing gonadal steroid output which method comprises administering to a mammalian subject an effective amount of a compound of the formula of claim 1 or a pharmaceutical composition therof.

22. A pharmaceutical composition for depression of spermatogenesis and circulating and testicular levels of testosterone comprising a compound of tne formula of claim 1 in admixture witn a pharmaceutically acceptable, non-toxic carrier.

23. A slow release pharmaceutical composition comprising a compound of claim 1 in the amount of 1% and a glycolide/lactide polymer in the amount of 99% in the form of microspheres or an implant.

* * * * *